(12) United States Patent
Wu et al.

(10) Patent No.: US 10,155,822 B2
(45) Date of Patent: Dec. 18, 2018

(54) PROCESS FOR PREPARATION OF A GRIFOLA FRONDOSA POLYSACCHARIDE F2 AND ITS HYPOGLYCEMIC ACTIVITY

(71) Applicants: Guangdong Institute of Microbiology, Guangzhou (CN); Guangdong Yuewei Edible Fungi Technology Co.,Ltd., Guangzhou (CN)

(72) Inventors: Qingping Wu, Guangzhou (CN); Chun Xiao, Guangzhou (CN); Yizhen Xie, Guangzhou (CN); Xiaobing Yang, Guangzhou (CN); Senzhu Li, Guangzhou (CN)

(73) Assignees: Guangdong Institute of Microbiology, Guangzhou (CN); Guangdong Yuewei Edible Fungi Technology Co., Ltd., Guangzhou (CN)

( * ) Notice: Subject to any disclaimer, the term of this patent is extended or adjusted under 35 U.S.C. 154(b) by 11 days.

(21) Appl. No.: 15/414,255

(22) Filed: Jan. 24, 2017

(65) Prior Publication Data
US 2017/0260299 A1  Sep. 14, 2017

Related U.S. Application Data

(63) Continuation of application No. 14/549,184, filed on Nov. 20, 2014.

(30) Foreign Application Priority Data

Dec. 25, 2013 (CN) .......................... 2013 1 0733480

(51) Int. Cl.
| | |
|---|---|
| *C08B 37/00* | (2006.01) |
| *C08L 5/00* | (2006.01) |
| *A61K 36/07* | (2006.01) |
| *A61K 31/715* | (2006.01) |

(52) U.S. Cl.
CPC ........ *C08B 37/0003* (2013.01); *A61K 31/715* (2013.01); *A61K 36/07* (2013.01); *C08B 37/006* (2013.01); *C08L 5/00* (2013.01); *A61K 2236/00* (2013.01)

(58) Field of Classification Search
CPC ...... C08B 37/0003; C08B 37/006; C08L 5/00
See application file for complete search history.

(56) References Cited

PUBLICATIONS

Kurushima et al., Mycoscience, 2000, 41, p. 473-480. (Year: 2000).*
Second CN Office Action of foreign priority CN application 201310733480.8.
Announcement of patent grant of foreign priority CN application 201310733480.8.
Notification of Patent Right Grant of foreign priority CN application 201310733480.8.
English response to second CN Office Action.
English CN granted claims.

* cited by examiner

*Primary Examiner* — Jonathan S Lau
(74) *Attorney, Agent, or Firm* — Wang Law Firm, Inc.

(57) ABSTRACT

A *Grifola frondosa* polysaccharide F2 with hypoglycemic activity, process for preparation and use thereof. The process for preparation of *Grifola frondosa* polysaccharide F2 is as follows: The fruit bodies of *Grifola frondosa* were homogenized to a fine powder and extracted with hot water. The mixture was filtered and precipitated with absolute ethanol. The precipitation was obtained. The said precipitation was applied on DEAE Sepharose Fast chromatographic column, equilibrated with Tris-HCl (10 mM, pH=8.0), collecting the efficient eluting peak to obtain the fraction F1; eluted with Tris-HCl (10 mM, pH=8.0) which contains 0.1M NaCl, fraction F2 was obtained; then concentrated under reduced pressure, dialyzed and lyophilized, *Grifola frondosa* polysaccharide F2 was obtained. This isolates a new *Grifola frondosa* polysaccharide F2 with hypoglycemic activity from the fruit bodies of *Grifola frondosa*. The *Grifola frondosa* polysaccharide F2 can be used in manufacturing a drug for treating diabetes. The polysaccharide makes a foundation for developing new anti-diabetes agents.

13 Claims, 6 Drawing Sheets

PROCESS FOR PREPARATION OF A GRIFOLA FRONDOSA POLYSACCHARIDE F2 AND ITS HYPOGLYCEMIC ACTIVITY

RELATED APPLICATION

This application is a continuation of U.S. Ser. No. 14/549184, filed on Nov. 20, 2014, which claims the benefit of Chinese Patent Application No. 201310733480.8, filed on Dec. 25, 2013, the specifications of which are incorporated herein with this reference.

TECHNICAL FIELD

This invention relates to a *Grifola frondosa* polysaccharide F2 with hypoglycemic activity, preparation method and use thereof, belonging to the field of bio-medicine.

BACKGROUND

Diabetes is a metabolic disorder syndrome characterized by hyperglycemia. The number of diabetes patients around the world has been increasing at a speed of 6 percent each year. Between 2010 and 2030, the number of adults with diabetes was expected to increase by 69% in developing countries and by 20% in developed countries. Diabetes includes type 1 and type 2 diabetes, with type 2 diabetes accounting more than 90% of all cases of diabetes. There is currently no known method to conquer diabetes, and the patients' conditions are generally controlled and alleviated by orally administered drugs for a long-term. But most of current drugs for diabetes are chemical or biochemical drugs, which have much side effects. Based on this critical situation, safer and more effective treatment modalities for diabetes are therefore needed to address the increase in prevalence of diabetes.

A polysaccharide with hypoglycemic activity was obtained from fruit body of cultivated *Grifola frondosa* by Xun Ma—α-glucan with a molecular weight of 400-450KD. In the process of isolating polysaccharides from fruit body of *Grifola frondosa*, Kubo obtained a glycoprotein after adding one volume of ethanol into the hot water extract to generate suspension and centrifugation. The glycoprotein named X-fraction (polysaccharide:protein=65:35), with a molecular weight of 5×105 D, showed a significant hypoglycemic activity. Structure analysis indicated that it was a β-1,6-glucan with α-1,4-branch.

The modern pharmacology studies reveals that blood serum glucose can be lowered through increasing insulin levels, regulating the activity of some enzymes related to glycometabolism and sequentially accelerating the glucose oxidation utilization, and through improving the insulin resistance or inhibition of glucose absorption.

The possible action mechanism of MT-α-glucan from the fruit body of *Grifola frondosa* was increasing sensitivity of insulin and improving insulin resistance of the surrounding tissue through increasing the number of insulin receptor. Water soluble extract FXM from *Grifola frondosa* potentially decreased blood serum glucose by improvement the insulin resistance. Glycoprotein SX from fruit body of *Grifola frondosa* can improve glucose tolerance and increase the body's sensitivity to insulin.

It has been found that *Grifola frondosa* and its active ingredients have obvious hypoglycemic activity, however, the compositions, structures and mechanisms of most bioactive hypoglycemic ingredients are not fully understood, due to the complex chemical structures. That directly hinders the process of developing new anti-diabetes agents.

CONTENTS OF THE INVENTION

The object of this invention is to provide a new *Grifola frondosa* polysaccharide F2 with hypoglycemic activity and preparation method thereof.

A process for preparation of the above-mentioned *Grifola frondosa* polysaccharide F2 comprising:
(a) The fruit bodies of *Grifola frondosa* are homogenized to a fine powder and extracted with hot water. The mixture was filtered and precipitated with absolute ethanol, and the resulting precipitate of is obtained;
(b) The said precipitation is applied on DEAE Sepharose Fast Flow chromatographic column, equilibrated with Tris-HCl (10 mM, pH=8.0), collecting the efficient eluting peak to obtain the fraction F1; eluted with Tris-HCl (10 mM, pH=8.0) which contains 0 1 M NaCl, fraction F2 is obtained; then concentrated under reduced pressure, dialyzed and lyophilized, *Grifola frondosa* polysaccharide F2 is obtained.

Preferably, the said precipitation in the step (a) is dissolved into hot water, filtered by a 0.45 μm millipore filter and then dialyzed in dialysis bag of 3000D for 24 h to yield crude polysaccharides solutions. The concentration of crude polysaccharide in the *Grifola frondosa* crude polysaccharides solution is adjusted, and then be used as the sample of chromatographic separation in the step (b).

The said polysaccharide F2 from *Grifola frondosa* has a molecular weight of $4.52 \times 10^5$ D. The contents of polysaccharides and protein are respectively 95.6% and 3.6%. The said polysaccharides is mainly consisted of glucose, mannose, xylose, galactose, and arabinose; the amino acids mainly comprises: proline(Pro), serine(Ser), aspartic acid (Asp), lysine(Lys), alanine(Ala), glutamic acid(Glu), threonine(Thr), glycine(Gly), arginine(Arg), leucine(Leu) and valine(Val). The said polysaccharide F2 is a β-heteropolysaccharides composed of uronic acids. Based on the above-mentioned parameters, there is no known analogous polysaccharide in the existing technology, that is to say, *Grifola frondosa* polysaccharide F2 of this invention is a new *Grifola frondosa* polysaccharide.

Pharmacology experiment in vivo showed that when diabetic rats were continuously intragastrical administered *Grifola frondosa* polysaccharide F2 for 7 days, FBG (fasting blood glucose) can be decreased significantly. The mechanism of lower blood glucose levels is mainly through improvement insulin resistance.

Accordingly, the second object of the invention is to provide the use of *Grifola frondosa* polysaccharide F2 in manufacturing a drug for the treatment of diabetes, especially for type 2 diabetes.

Another object of the invention is to provide a drug for the treatment of diabetes, characterized in that the drug comprises *Grifola frondosa* polysaccharide F2 as active ingredients. The said diabetes is type 2 diabetes.

This invention isolates a new *Grifola frondosa* polysaccharide F2 with hypoglycemic activity from the fruit body of *Grifola frondosa*. It can be used in manufacturing a drug for the treatment of diabetes, especially for type 2 diabetes. The invention makes a foundation for developing new anti-diabetes agents in the future, and actively promotes the study on active ingredients of natural medicine for treating diabetes.

EXAMPLES

The examples below further illustrate the invention, rather than limiting the scope thereof.

Example 1

I. Preparation of *Grifola frondosa* Polysaccharide F2

The fruit bodies of *Grifola frondosa* were homogenized to a fine powder and extracted with hot water(5000 mL, 80° C.) for 8 hours. The mixture was filtered and the filtrate was concentrated to 1000 mL under reduced pressure, then precipitated with 4 volume of absolute ethanol. The precipitation was obtained by centrifugation at a speed of 5000 rpm. The precipitation was dissolved into hot water, filtered by a 0.45 μm millipore filter and dialyzed in dialysis bag of 3000 D for 24 h to yield crude polysaccharides solution. Finally the concentration of the solution was adjusted to be 10 mg/mL.

Figure 1:
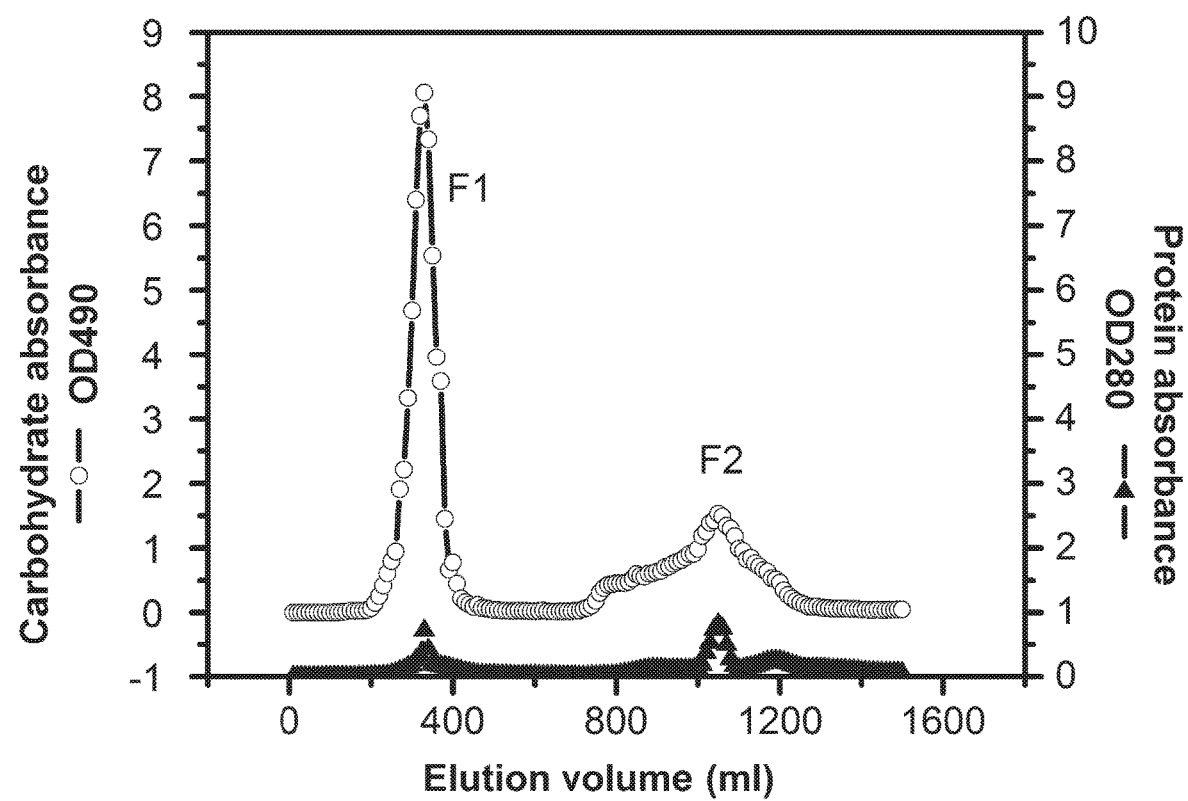
FIG. 1 shows the elution curve of the precipitation on DEAE Sepharose Fast Flow chromatography.

The above-mentioned crude polysaccharides solution (100 mL) was filtrated and applied on DEAE Sepharose Fast Flow chromatographic column (4.5×30 cm), F1 was obtained by collecting and concentrating the fraction equilibrated with 300 mL Tris-HCl (10 mM, pH=8.0), F2 was obtained by collecting and concentrating this fraction eluted with 300 mL Tris-HCl buffer (10 mM, pH=8.0) which contains 0.1 M NaCl. The elution curve was shown in FIG. 1.

II. Determination of Purity and Molecular Weight of *Grifola frondosa* Polysaccharide F2

*Grifola frondosa* polysaccharide F2 (10 mg) was dissolved into the ultrapure water (1 mL) and analyzed by HPLC.

Chromatographic conditions: TSK-GEL G3000SW column(300 mm×718 mm); column temperature: 35° C.; mobile phase: 0.05M NaH$_2$PO$_4$-Na$_2$HPO$_4$ buffer (pH 6.7) containing 0 05% NaN$_3$; flow rate: 0.5 mL/min; differential refractive index detector and constant temperature at 35° C.; injection volume: 20 μL.

Figure 2:
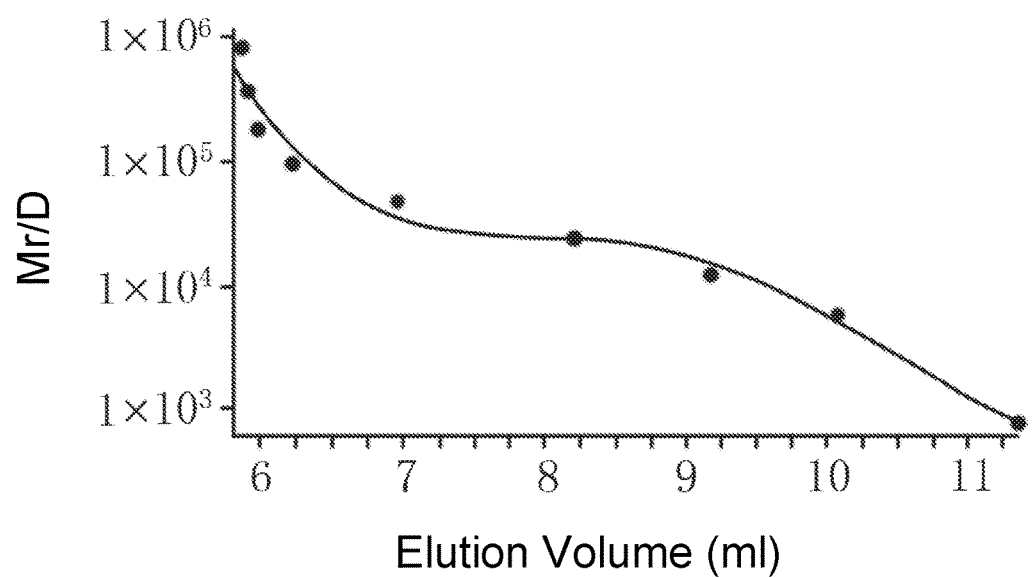
FIG. 2 shows the calibration curve of the standard polysaccharides on Gel permeation chromatography.

Establishment GPC calibration curve:10 mg polysaccharides with Mr of 738, 5800, 1.22×10$^4$, 2.37×10$^4$, 4.80×10$^4$, 1.00×10$^5$, 1.86×10$^5$, 3.80×10$^5$, 8.53×10$^5$ D were used as standards, dissolved into 0.05M NaH$_2$PO$_4$—Na$_2$HPO$_4$ buffer (1 mL, pH 6.7) containing 0 05% NaN$_3$, filtered by a 0.45 μm millipore filter and analyzed by GPC. The retention times of the standard polysaccharides with the known Mr were shown in table 1. GPC calibration curve was established with elution volume of the standard polysaccharides as the abscissa and the value of Mr as the vertical coordinates, see FIG. 2.

Figure 3:
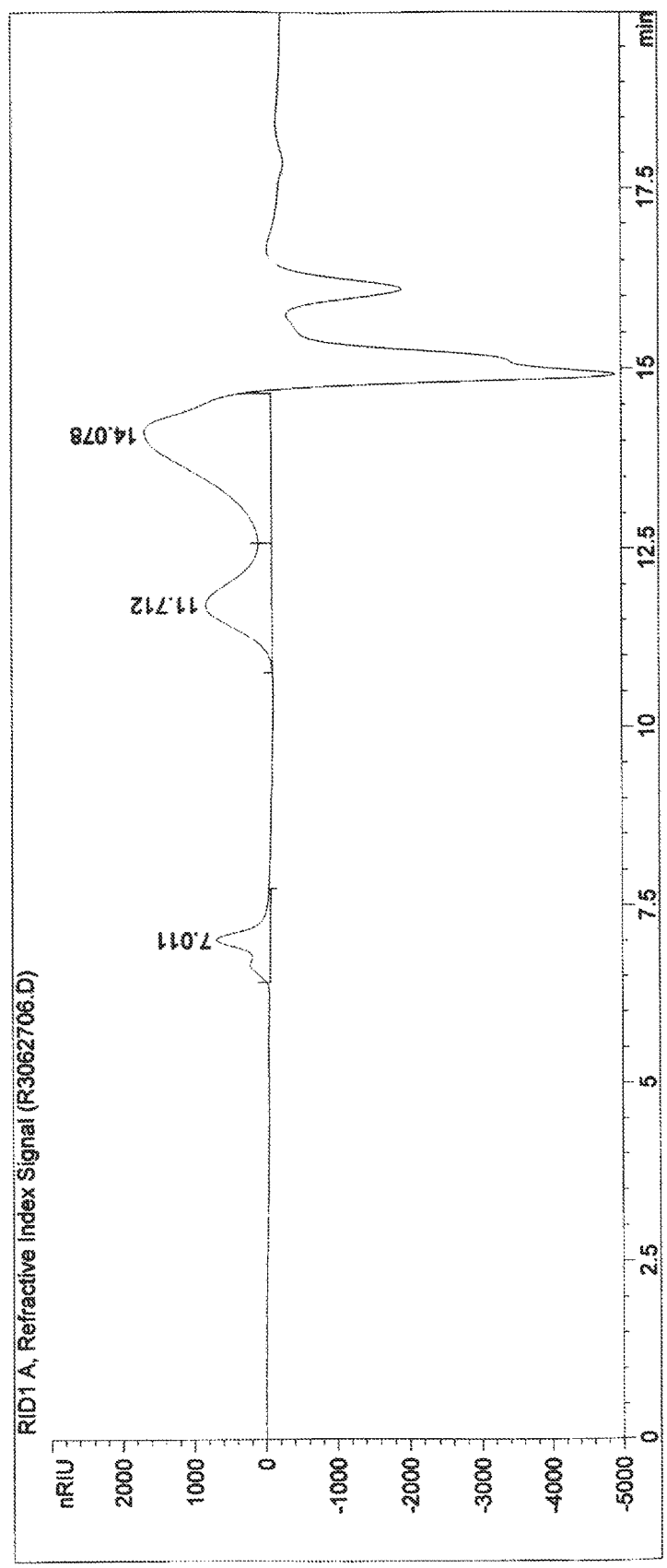
FIG. 3 shows the HPLC chromatogram of *Grifola frondosa* polysaccharide F2.

Determination of purity and molecular weight of *Grifola frondosa* polysaccharide F2: 10 mg *Grifola frondosa* polysaccharide F2 was dissolved in 0.05M NaH$_2$PO$_4$—Na$_2$HPO$_4$ buffer (1 mL, pH 6.7) containing 0 05% NaN$_3$, filtered by a 0.45 μm millipore filter and analyzed by GPC. The average molecular weight of *Grifola frondosa* polysaccharide F2 is 4.52×10$^5$D (as shown in FIG. 3), calculated automatically by GPC chromatographic working station.

TABLE 1

| The retention times of standard polysacchrides | | |
|---|---|---|
| Mr (D) | Retention time (min) | Elution volume (mL) |
| 738 | 22.6 | 11.3480 |
| 5800 | 20.1 | 10.4296 |
| 1.22 × 10$^4$ | 18.3 | 9.4976 |
| 2.37 × 10$^4$ | 16.3 | 8.4592 |
| 4.80 × 10$^4$ | 13.8 | 7.0456 |
| 1.00 × 10$^5$ | 12.3 | 6.1120 |
| 1.86 × 10$^5$ | 11.9 | 5.7824 |
| 3.80 × 10$^5$ | 11.7 | 5.6615 |
| 8.53 × 10$^5$ | 11.7 | 5.6416 |

III. Physicochemical Property of *Grifola frondosa* Polysaccharide F2

1. Determination of the Contents of Polysaccharides and Protein

The content of polysaccharides of F2 is 95.6% determined by phenol sulfuric acid method, and that of protein is 3.6% determined by Bradford method.

2. Amino Acid Composition Analysis

HPLC (HP1050, America), consisted of quaternary gradient pump, automatic sampler, column oven and HP1046A fluorescence detector; Full-automatic high Speed Freezing Centrifuge (2000 rpm, GL20A, Japan).

Standard amino acid, derivatization reagent OPA, FMOC from SIGMA firm; Na$_2$HPO$_4$ was of analytical grade; methyl alcohol and acetonitrile were of HPLC grade.

Chromatographic conditions: Hypersil ODS column (4.0×125 mm, particle size 5 μm); mobile phase (A): 10 mmol·L$^{-1}$ pH 7.2 Na$_2$HPO$_4$buffer (PB); mobile phase (B): the mixture of PB, methyl alcohol and acetomitrile (volume percents of them were respectively 50%, 35% and 15%); linear gradient: volume fraction of mobile phase B rise to 40% from 0% linearly in 0-10min; volume flow rate: 1.0 mL·min$^{-1}$; column temperature: 40° C.; determine wavelength: excitation wavelength 340 nm and emission wavelength 450 nm.

Samples Treatments:

Standard solution: standard amino acids were dissolved into 0.1 mol·L$^{-1}$HCl solution, and diluted to standard solution, in which the concentration of each amino acid was 250 nM.

Hydrolysis: putting *Grifola frondosa* polysaccharide F2 into a hydrolysis tube, adding 6 M HCl (10~15 mL) and two drops of newly-distilled phenol. The hydrolysis tube was freezed for 3-5 min in refrigerant, and then linked to the exhaust tube of vacuum pump. Vacuum pumping to be closed to 0 Pa and filling with high-purity nitrogen, the treatment was repeated three times and the hydrolysis tube was sealed under nitrogen. The sealed hydrolysis tube was put into a constant temperature drying oven (110±1° C.), after 23 hours, taken out and cooled. Opening and washing the hydrolysis tube with deionized water, all the hydrolysate was transferred into a 100 mL volumetric flask and diluted with deionized water to volume. The hydrolysate was properly diluted to be detected.

Contrasting to HPLC chromatogram of the standard amino acids, it was inferred that the amino acids of *Grifola frondosa* polysaccharide F2 mainly comprises: proline(Pro), serine(Ser), aspartic acid(Asp), lysine(Lys), alanine(Ala), glutamic acid(Glu), threonine(Thr), glycine(Gly), arginine (Arg), leucine(Leu) and valine(Val). See table 2.

TABLE 2

Amino acid composition of *Grifola frondosa* polysaccharide F2

| Analysis items | Results | Unit |
|---|---|---|
| Phenylalanine (Phe) | <0.10 | g/100 g |
| Alanine (Ala) | 0.19 | |
| Methionine (Met) | <0.10 | |
| Proline (Pro) | 0.38 | |
| Glycine (Gly) | 0.15 | |
| Glutamic acid (Glu) | 0.19 | |
| Arginine (Arg) | 0.11 | |
| Lysine (Lys) | 0.19 | |
| Tyrosine (Tyr) | <0.10 | |
| Leucine (Leu) | 0.10 | |
| Serine (Ser) | 0.23 | |
| Threonine (Thr) | 0.17 | |
| Aspartic acid (Asp) | 0.21 | |
| Isoleucine (Ile) | <0.10 | |
| Histidine (His) | <0.10 | |
| Valine (Val) | 0.10 | |
| Total | 2.1 | |

3. Monosaccharide Composition of *Grifola frondosa* Polysaccharide F2 Analysis by GC-MS Hydrolysis: *Grifola frondosa* polysaccharide F2 was dissolved in 2 M $H_2SO_4$, heated to reflux for 6 hours, cooled and then neutralized with saturated Ba $(OH)_2$ to be neutral. The mixed liquid was filtrated and the filtrate was collected.

Acetylation: the above-mentioned hydrolysate was evaporated to dryness. The residue sample was converted to acetylated derivatives with 70 mg hydroxylamine hydrochloride and 5 mL pyridine for 1 hour at 90° C. by water bath heating. After slightly cooling, 5 mL acetic anhydride was then added with heating at 90° C. After 1 hour, 10 mL water was added to break the anhydride and the acetylated products was extracted with chloroform. The extract liquor was washed with water and then subsequently dehydrated with anhydrous $Na_2SO_4$. The supernate was concentrated to 1 mL under nitrogen and analyzed by using GC-MS.

GC-MS operation conditions: SE230 elastic quartz capillary column (15 m×012 mm×0133 Lm); the temperature program was set to increase to 280° C. from 100° C. at a rate of 10° C./min, then holding for 10min at 280° C.; carrier gas: Helium; column pressure: 70 kPa; split ratio: 10:1; solvent delay: 2 min; electron ionization mode: EI; electron energy: 70 eV; quadrupole rod temperature: 150° C.; temperature of ion source: 230° C.; voltage of electron multiplier: 2300V; interface temperature of GC-MS: 280° C.; Mass scanned range (m/z): 29-500.

The monosaccharide composition of *Grifola frondosa* polysaccharide F2 was analyzed by GC-MS after hydrolysis and acetylation, as control, the standard monosaccharides was acetylated simultaneously. According to the total ions chromatogram of standard monosaccharides, it can be inferred that *Grifola frondosa* polysaccharide F2 is a heteropolysaccharide mainly consisted of glucose, mannose, xylose, galactose, arabinose and ribose. The relative content of the monosaccharides were shown in table 3.

TABLE 3

Monosaccharide composition of *Grifola frondosa* polysaccharide F2

| Sample Names | Monosaccharide Composition | Relative content by peak area normalization (%) | Methods |
|---|---|---|---|
| *Grifola frondosa* polysaccharide F2 | Ribose | 1.96 | The samples were analyzed by GC-MS after hydrolysis and acetylation |
| | Arabinose | 3.22 | |
| | Xylose | 8.02 | |
| | Mannose | 16.72 | |
| | Glucose | 63.74 | |
| | Galactose | 6.75 | |

4. Infrared Spectrum(IR) Analysis of *Grifola frondosa* Polysaccharide F2

Figure 4:
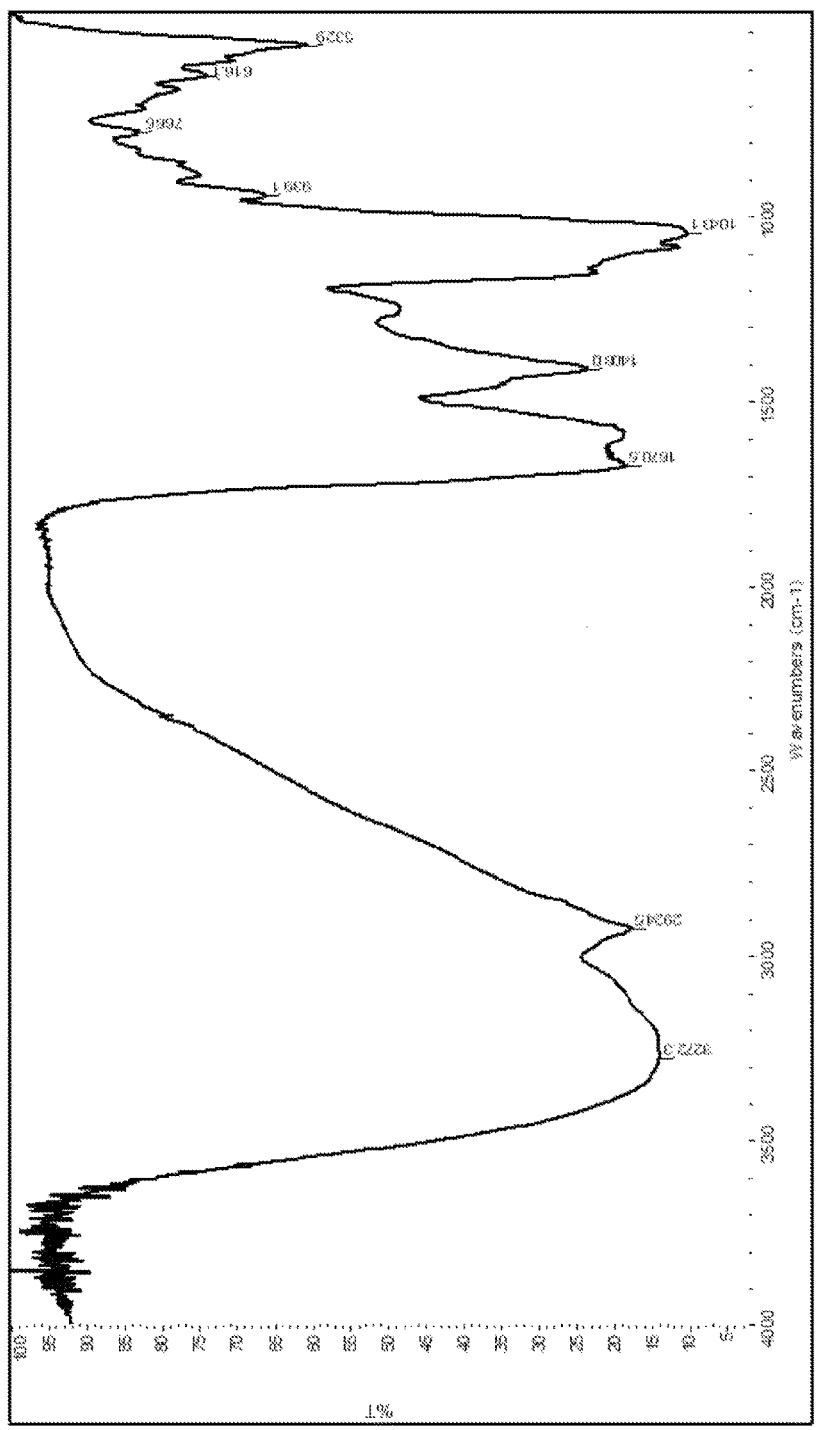
FIG. 4 shows the Infrared spectrum (IR) of *Grifola frondosa* polysaccharide F2.

1 mg of *Grifola frondosa* polysaccharide F2 and 100 mg of dried KBr were porphyrizied and tabletted, the infrared profile of *Grifola frondosa* polysaccharide F2 was scaned in the range of 400 to 4000 $cm^{-1}$. Table 4 was the analysis of absorption peaks in the infrared spectrum (FIG. 4). According to the infrared spectrum analysis, *Grifola frondosa* polysaccharide F2 is mainly consisted of pyranoid rings linked by β-glucosidic bonds.

TABLE 4

Analysis of absorption peaks in the infrared spectrum of *Grifola frondosa* polysaccharide F2

| Number | Wavenumber ($cm^{-1}$) | Transmittance (%) | Analysis of the peaks |
|---|---|---|---|
| 1 | 3272.3 | 15 | hydroxy |
| 2 | 2924.5 | 16 | Stretching vibration of C—H |
| 3 | 1670.5 | 18 | Stretching vibration of C=O |
| 4 | 1408 | 20 | Stretching vibration of $COO^-$ |
| 5 | 1064 | 10 | pyranoid rings linked by β-glucosidic bonds |
| 6 | 885-900 | | β-glucosidic bonds |

Figure 5:
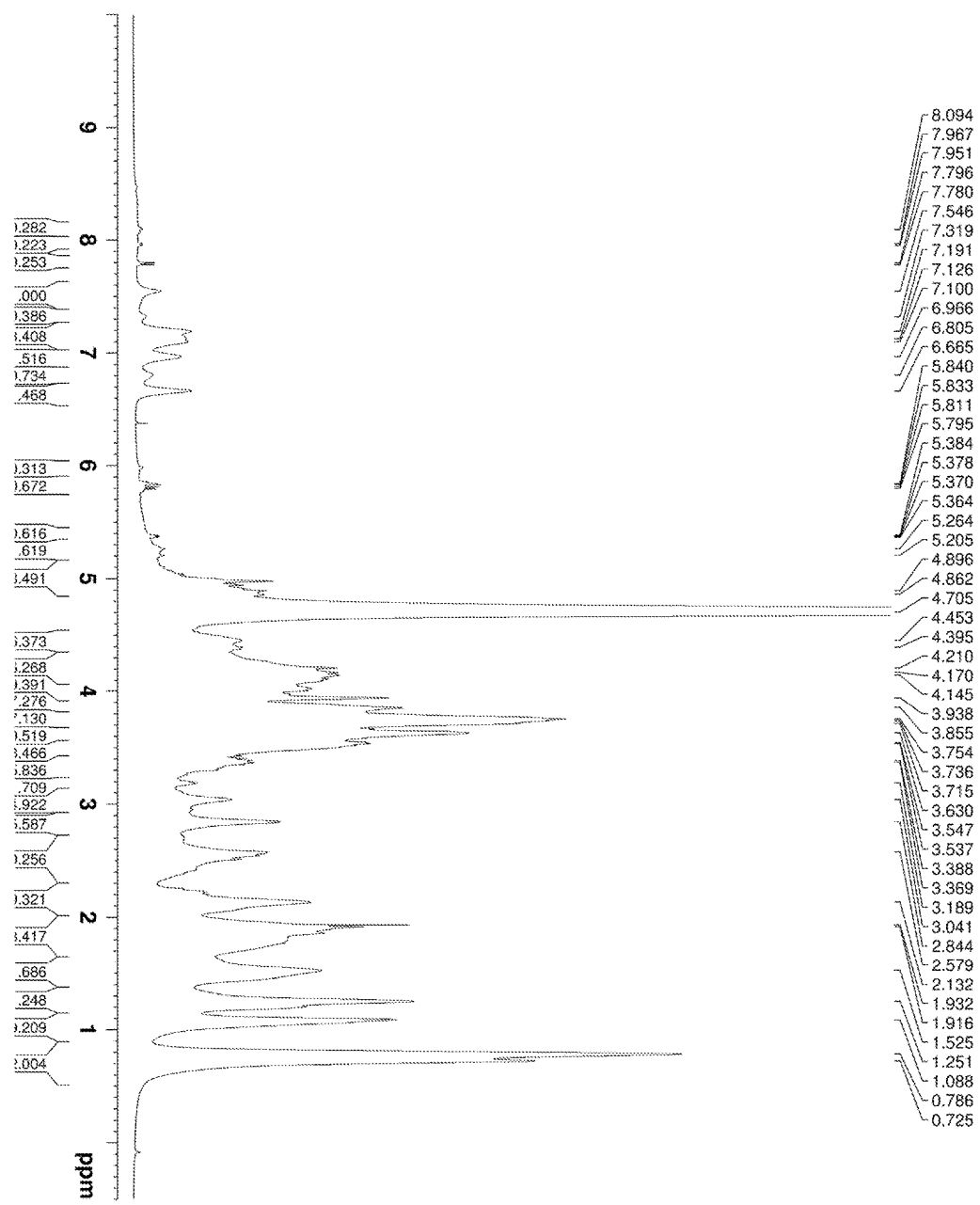
FIG. 5 shows the $^1$H-NMR spectrum of *Grifola frondosa* polysaccharide F2.
Figure 6:
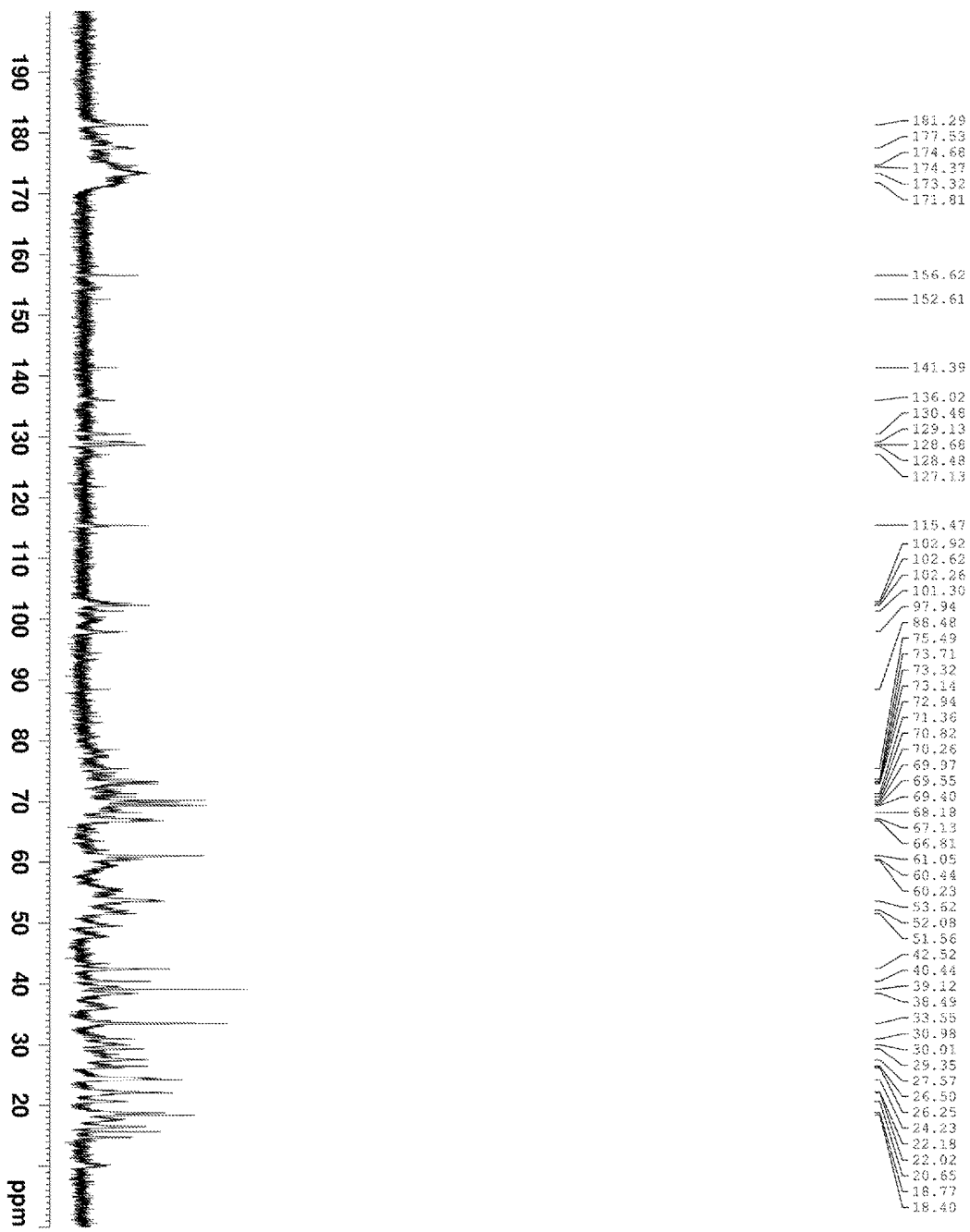
FIG. 6 shows the $^{13}$C-NMR spectrum of *Grifola frondosa* polysaccharide F2.

5. NMR Spectrum of *Grifola frondosa* Polysaccharide F2: $^1$H-NMR and $^{13}$C-NMR The $^1$H-NMR spectr of *Grifola frondosa* polysaccharide F2 was shown in FIG. 5 and the $^{13}$C-NMR spectrum in FIG. 6.

The signal at 4.395 ppm of $^1$H-NMR indicated that *Grifola frondosa* polysaccharide F2 is mainly consisted of pyranoid rings, in accordance with the results from infrared spectrum analysis.

In $^{13}$C-NMR, the chemical shifts of anomeric carton are generally in the range of 90-110 ppm, and the number of glycoside residues depends on the number of signal peaks. So *Grifola frondosa* polysaccharide F2 is consisted of five glycoside residues. The results of GC-MS showed it contains six glycoside residues, wherein the fraction of ribose is just 1.96%, thus, *Grifola frondosa* polysaccharide F2 is mainly consisted of glucose, mannose, xylose, galactose, and arabinose.

According to $^{13}$C-NMR, the number of glycoside residues and their relative contents can be determined by the number of peaks in the resonance area of anomeric carton (90-110 ppm). In general, the chemical shifts of anomeric carbons from α-glucosides are in the range of 95-101 ppm, while that of β-glucosides in the range of 101-105 ppm. The chemical shifts of *Grifola frondosa* polysaccharide F2 are respectively at 97.94 ppm, 101.30 ppm, 102.26 ppm, 102.92 ppm and 115.47 ppm, it is consequently considered as a β-heteropolysaccharide.

In addition, the characteristic signals of $^{13}$C-NMR can determine some glycoside residues and groups, for example, the signals of carboxyls-C of uronic acids are in the range of 170-180 ppm, and the chemical shifts of *Grifola frondosa* polysaccharide F2 are respectively at 171.81 ppm, 173.32 ppm, 174.37 ppm, 177.68 ppm and 177.53 ppm, as a consequence, *Grifola frondosa* polysaccharide F2 contains uronic acids.

In conclusion, *Grifola frondosa* polysaccharide F2 of the invention has a molecular weight of $4.52 \times 10^5$ D. The contents of polysaccharides and protein are respectively 95.6% and 3.6%. The said polysaccharides is mainly consisted of glucose, mannose, xylose, galactose, and arabinose; the amino acids mainly comprises: proline(Pro), serine(Ser), asparitic acid(Asp), lysine(Lys), alanine(Ala), glutamic acid (Glu), threonine(Thr), glycine(Gly), arginine(Arg), leucine (Leu) and valine(Val). The said polysaccharide F2 is a β-pyran heterocyclic polysaccharide containing uronic acids. Based on the above-mentioned parameters, there is no known analogous polysaccharide in the existing technology. Therefore, *Grifola frondosa* polysaccharide F2 of this invention is a new *Grifola frondosa* polysaccharide.

IV. Pharmacology Experiment

Hypoglycemic experiment of *Grifola frondosa* polysaccharide F2 on type 2 diabeticrats:

(1) Induction of diabetes rats: SD rats at age of 6 weeks (weight: 140-160 g), male, were marked and kept in separate cages. They were adapted for 7 days and then fasted overnight before an intraperitoneal injection of freshly prepared STZ (Sigma, 35 mg/kg body weight [BW], dissolved in citrate buffer, pH 4.5). Then, the rats were fed a high-fat diet. After 4 weeks, the rats were fasted for 5 h and fasting serum glucose levels were determined. Rays with fasting serum glucose levels >11.1 mM were considered to be diabetic and were used in the study.

(2) Assessment of hypoglycemic activity: Except normal control (NC), the diabetic rats (DM) were randomly divided into three groups: 1. model control group (MC); 2. low-dose group of *Grifola frondosa* polysaccharide F2 (50 mg/kg BW, Intragastric(ig)); 3. high-dose group of *Grifola frondosa* polysaccharide F2 (100 mg/kg BW, Intragastric(ig)). The rats of low-dose and high-dose groups were administered different doses of *Grifola frondosa* polysaccharide F2 by intragastric infusion, meanwhile, rats of NC and MC were administered saline. The blood glucose levels were measured after continuously giving drugs for 2 weeks. According to table 5, FBG were decreased significantly (*P<0.05) after diabetic rats were continuously administered *Grifola frondosa* polysaccharide F2 (100 mg/kg BW) for 2 weeks by intragastric infusion. Thus, *Grifola frondosa* polysaccharide F2 of the invention can be used to manufacture medicaments for the treatment of diabetes, especially for type 2 diabetes.

TABLE 5

Effects of *Grifola frondosa* polysaccharide F2 on FBG in type 2 diabetic rats(ig).

| Groups | Dose (mg/kg/d) | Fasting Serum Glucose FSG(mmol/L) | | |
|---|---|---|---|---|
| | | 0 w | 1 w | 2 w |
| NC | / | 5.68 ± 0.39 | 5.78 ± 0.61 | 5.94 ± 0.42 |
| MC | / | 20.65 ± 4.56 | 25.22 ± 3.94 | 24.77 ± 4.27 |
| F2 | 50 | 21.41 ± 4.29 | 23.74 ± 2.67 | 23.43 ± 2.98 |
| F2 | 100 | 21.41 ± 4.23 | 23.62 ± 2.97 | 21.03 ± 3.19* | ps: compared to MC:
*P < 0.05,
** P < 0.01.

The invention claimed is:

1. A process for perparing *Grifola frondosa* polysaccharide F2 (GFPF2), the process comprising:
   (a) homogenizing fruit bodies of *Grifola frondosa* to a fine powder and extracting the fine powder with hot water to obtain a mixture; filtering the mixture to obtain a mixture filtrate and precipitating the mixture filtrate with ethanol to obtain a precipitate, which is dissolved, filtered, dialyzed, and concentrated to form a sample, and
   (b) loading the sample onto a DEAE Sepharose Fast chromatographic column, equilibrating the loaded column with a Tris-HCI buffer, collecting the efficient eluting peak to obtain the fraction F1; eluting with a Tris-HCI buffer which contains 0.1 M NaCl to obtain fraction F2, and concentrating F2 under reduced pressure followed by dialysis and lyophilization to obtain the GFPF2.

2. The process of claim 1, wherein the precipitate obtained in step (a) is
   dissolved into hot water,
   filtered through a 0.45 µm millipore filter,
   dialyzed in dialysis bag of 3000 D for 24 h; and
   concentrated before being used in step (b).

3. The process of claim 1, wherein the precipitate obtained in step (a) is
   dissolved into hot water and filtered through a 0.45 µm millipore filter.

4. The process of claim 1, wherein the precipitate obtained in step (a) is
   dissolved into hot water, filtered through a 0.45 µm millipore filter,
   dialyzed in dialysis bag of 3000 D for 24 h.

5. The process of claim 1, wherein the GFPF2 has a molecular weight of $4.5 \times 10^5$ Dalton and comprises about 95.6% of polysaccharide.

6. The process of claim 5, wherein the polysaccharide consists essentially of ribose, glucose, mannose, xylose, galactose, and arabinose.

7. The process of claim 5, wherein the polysaccharide is a β-heteropolysaccharide that comprises uronic acids.

8. The process of claim 1, wherein the GFPF2 comprises protein that comprises proline(Pro), serine(Ser), asparitic acid(Asp), lysine(Lys), alanine(Ala), glutamic acid(Glu), threonine(Thr), glycine(Gly), arginine(Arg), leucine(Leu), valine(Val), phenylalanine (Phe), methionine (Met), tyrosine (Tyr), isoleucine (Ile), and histidine (His).

9. A process for preparation of *Grifola frondosa*polysaccharide F2 (GFPF2), comprising:
   (a) homogenizing the fruit bodies of *Grifola frondosa* to a fine powder and extracting the fine powder with hot water to obtain a mixture; filtering the mixture to obtain a mixture filtrate and precipitating the mixture filtrate with 4-volume ethanol to obtain a precipitate, and
   (b) loading the precipitate onto a DEAE Sepharose Fast chromatographic column, equilibrating the loaded column with 10 mM, pH=8.0 Tris-HCI buffer, collecting the efficient eluting peak to obtain the fraction F1; eluting with 10 mM, pH=8.0 Tris-HCI buffer which contains 0.1 M NaCI to obtain fraction F2 and concentrating F2 under reduced pressure followed by dialysis and lyophilization to obtain the GFPF2;

wherein the precipitate obtained in step (a) is dissolved into hot water, filtered by a 0.45 μm millipore filter, dialyzed in dialysis bag of 3000 D for 24 h concentrated before being used in step (b).

10. The process of claim 9, wherein the GFPF2 has a molecular weight of $4.5 \times 10^5$ Dalton and comprises about 95.6% of polysaccharide.

11. The process of claim 10, wherein the polysaccharide consists essentially of ribose, glucose, mannose, xylose, galactose, and arabinose.

12. The process of claim 10, wherein the polysaccharide is a β-heteropolysaccharide that comprises uronic acids.

13. The process of claim 9, wherein the GFPF2 comprises protein that comprises proline(Pro), serine(Ser), asparitic acid(Asp), lysine(Lys), alanine(Ala), glutamic acid(Glu), threonine(Thr), glycine(Gly), arginine(Arg), leucine(Leu), valine(Val), phenylalanine (Phe), methionine (Met), tyrosine (Tyr), isoleucine (Ile), and histidine (His).

* * * * *